United States Patent [19]
Kenley et al.

[11] Patent Number: 6,146,523
[45] Date of Patent: *Nov. 14, 2000

[54] USER INTERFACE AND METHOD FOR CONTROL OF MEDICAL INSTRUMENTS, SUCH AS DIALYSIS MACHINES

[75] Inventors: Rodney S. Kenley, Libertyville; Dawn Matthews, Grayslake; Douglas L. Wilkerson, Gurnee; Joel DeJesus, Buffalo Grove; Tom L. Brose, Gurnee; Andrew Gebhardt, Lake Zurich; Lori A. Plummer, Spring Grove; Frederick H. Peter, Jr., Barrington; Russel L. Sage, McHenry; Dennis M. Treu, Gurnee, all of Ill.; Michael Edward Wiklund, Concord; William R. Dolan, Newtonville, both of Mass.; Shawn O. Barrett, Grayslake, Ill.

[73] Assignee: Aksys, Ltd., Lincolnshire, Ill.

[*] Notice: This patent is subject to a terminal disclaimer.

[21] Appl. No.: 09/128,185

[22] Filed: Aug. 3, 1998

Related U.S. Application Data

[63] Continuation of application No. 08/800,405, Feb. 14, 1997, Pat. No. 5,788,851, which is a continuation-in-part of application No. 08/559,933, Feb. 5, 1996, Pat. No. 5,674,397, which is a division of application No. 08/388,275, Feb. 13, 1995, Pat. No. 5,591,344, and a continuation-in-part of application No. 29/052,303, Apr. 1, 1996, Pat. No. Des. 383,842.

[51] Int. Cl.⁷ ............................. B01D 61/30; B01D 61/32
[52] U.S. Cl. ....................... 210/143; 210/321.6; 210/646; 248/919; 345/173; 604/4
[58] Field of Search .................. 210/87, 321.67, 210/321.71, 416.1, 541, 646, 647, 929, 143; 604/4, 5, 6; 248/919, 920; 345/173, 205, 326, 905

[56] References Cited

U.S. PATENT DOCUMENTS

| | | |
|---|---|---|
| 4,756,706 | 7/1988 | Kerns et al. .............................. 604/66 |
| 4,804,950 | 2/1989 | Moon et al. ............................. 340/712 |
| 4,873,623 | 10/1989 | Lane et al. . |
| 4,898,578 | 2/1990 | Rubalcalba, Jr. . |
| 4,914,624 | 4/1990 | Duthorn .................................. 340/712 |
| 4,942,514 | 7/1990 | Miyagaki et al. . |
| 5,056,059 | 10/1991 | Tivig et al. ............................. 340/712 |
| 5,108,063 | 4/1992 | Koerber et al. ......................... 248/917 |
| 5,187,641 | 2/1993 | Muskatello et al. .................... 361/682 |
| 5,247,434 | 9/1993 | Peterson et al. . |
| 5,326,476 | 7/1994 | Grogan et al. .......................... 210/646 |
| 5,330,415 | 7/1994 | Storti et al. ............................. 248/919 |
| 5,472,614 | 12/1995 | Rossi . |
| 5,487,827 | 1/1996 | Petersen et al. .......................... 210/87 |
| 5,591,344 | 1/1997 | Kenley et al. ........................... 210/646 |

(List continued on next page.)

FOREIGN PATENT DOCUMENTS

| | | |
|---|---|---|
| 0186973 | 7/1986 | European Pat. Off. . |
| 2110564 | 6/1983 | United Kingdom . |
| 2205669 | 12/1988 | United Kingdom . |

*Primary Examiner*—Joseph W. Drodge
*Attorney, Agent, or Firm*—McDonnell Boehnen Hulbert & Berghoff

[57] ABSTRACT

A user interface for a medical instrument such as a dialysis machine is described which uses both a touch screen and at least one hard key off of the touch screen to effectuate a change in a parameter associated with the operation of the machine or the treatment session. The user interface is connected to a central computer control system having a host microprocessor and a backup safety microprocessor. The hard key is directly wired to the safety microprocessor. After the user selects a new parametric value on the touch screen, the user presses a hard key. The host and safety microprocessors implement a verification routine to insure that the entered parameter is appropriate for the patient's treatment and the display on the touch screen. If the verification procedure ends in a positive result, the user is prompted to presses a second hard key to confirm the change, causing an additional verification check to be preformed. If the additional verification check is successful, the parametric value is entered into a memory (such as a hard disk) storing instructions for operation of the medical instrument.

8 Claims, 6 Drawing Sheets

U.S. PATENT DOCUMENTS

| | | | |
|---|---|---|---|
| 5,609,770 | 3/1997 | Zimmerman et al. | 210/646 |
| 5,618,441 | 4/1997 | Rosa et al. | 210/646 |
| 5,620,608 | 4/1997 | Rosa et al. | 210/646 |
| 5,629,871 | 5/1997 | Love et al. | 210/646 |
| 5,746,708 | 5/1998 | Giesler et al. | 604/4 |
| 5,788,851 | 8/1998 | Kenley et al. | 210/739 |
| 5,824,213 | 10/1998 | Utterberg | 210/646 |
| 5,895,571 | 4/1999 | Utteberg | 210/646 |
| 5,919,153 | 7/1999 | Van Driel | 604/4 |

USER INTERFACE AND METHOD FOR CONTROL OF MEDICAL INSTRUMENTS, SUCH AS DIALYSIS MACHINES

RELATED APPLICATIONS

This is a continuation of application Ser. No. 08/800,405, filed Feb. 14, 1997, now U.S. Pat. No. 5,788,851. Which is a continuation-in-part of application Ser. No. 08/559,933 filed Feb. 5, 1996, now U.S. Pat. No. 5,674,397, which is a divisional of application of Kenley et al., Ser. No. 08/388,275 filed Feb. 13, 1995, now U.S. Pat. No. 5,591,344. This is also a continuation in part of application Ser. No. 29/052,303 filed Apr. 1, 1996, now U.S. Pat. No. D383,842.

NOTICE REGARDING COPYRIGHT

A portion of the disclosure of this patent document contains matter subject to copyright protection. The copyright owner has no objection to the facsimile reproduction by anyone of the patent disclosure, as it appears in the Patent and Trademark Office files and records, but otherwise retains all copyright rights whatsoever.

BACKGROUND OF THE INVENTION

A. Field of the Invention

This invention relates to the field of medical instruments and their user interfaces, and more particularly to a user interface and control method for a medical instrument such as a dialysis machine.

B. Description of Related Art

Dialysis machine are used for treating patients with inadequate kidney function. Hemodialysis machines typically include, among other things, an extracorporeal blood circuit comprising an arterial line, a blood pump, a dialyzer having a semipermeable membrane and a venous line. Blood is removed from the patient and pumped by the blood pump through the arterial line to the blood compartment of the dialyzer, where toxins and excess water are removed from the patient's blood. A dialysate solution is circulated on the other side of the membrane and carries away the toxins and removed water. The blood is then returned to the patient via the venous line. Peritoneal dialysis machines prepare a dialysate solution which is introduced into the patient's peritoneal cavity.

Dialysis machines typically have some sort of controls to regulate the operation of the machine. Such controls in the past were a rather unattractive and hard to use set of dials and switches that required trained medical professionals to use properly. More contemporary machines have a single user interface to allow a patient or medical practitioner to interact with the machine and adjust machine operation or treatment parameters, e.g., blood pump rate, dialysate temperature or flow rate, treatment time, heparin pump rate, etc.

The patent to Grogan et al., U.S. Pat. No. 5,326,476, which is incorporated by reference herein, describes a touch screen that is used to control the operation of a hemodialysis machine. The touch screen is connected to a host microprocessor which controls operation of most of the active components of the machine. When the user wishes to change a treatment parameter, the user touches an icon on the touch screen and a key pad with an enter key pops up on the screen. The user enters the new value by touching the numbers on the key pad and pressing the enter button on the key pad. A verify button is then pressed on the touch screen if the user wishes to confirm the change. The patent also briefly describes a method of touching the touch screen to program a time-varying parameter, such as ultrafiltration removal over the course of a dialysis session.

User interfaces that solely depend on a touch screen as a means for entering and confirming parametric values, such as described in the Grogan et al. patent, are vulnerable to failures in the touch screen display. If the touch screen is defective, the computer system may not receive the correct information from the touch screen or interpret the information incorrectly. The present invention was designed to provide for redundancy and safety verification of parametric value changes independent of the operation of the touch screen, and thereby avoid accidental or unintended changes of parameters in the event of a defect in the touch screen.

The user interface of the present invention provides for the combination of a touch screen, and at least one hard key that are separate and apart from the touch screen, whereby both the touch screen and the hard keys have to be pressed to enter and verify a change in a parametric value pertinent to the treatment or the operation of the machine. The computer control system for the machine also uses host and safety backup microprocessors which are responsive to the touch screen and hard keys to perform internal verification and confirmation checking procedures to verify that the change in parametric value requested by the user is proper. These features combine to offer safety benefits, robustness, and ease of use that are believed to be superior to user interfaces known in the prior art.

Another object of the invention is to provide a user interface design for a medical instrument that is especially easy to use by a person that is not a technically trained medical professional, i.e., by the patient or a member of the patient's family.

SUMMARY OF THE INVENTION

A system for controlling the operation of a dialysis machine is provided comprising in combination a user interface and a central computer control system. The user interface comprises a touch screen that displays messages and information as to the machine status to a user, and permits the user to touch the touch screen to select parametric values pertinent to operation of the machine. The user interface further includes at least one hard key off of the touch screen. The touch screen prompts the user to press the hard key to signify that the selection of the parametric value by the user has been completed.

The central computer control system controls operation of the machine and is responsive to the touch screen and the hard key. The control system comprises a host central processing unit and a safety central processing unit (both comprising microprocessors) operatively connected to each other so as to enable an exchange of information related to the selected parametric value.

When the user presses the hard key to indicate that the selection process is complete, this action causes the host and safety microprocessors to undergo a verification routine whereby the selected parametric value is checked for appropriateness for a patient connected to the machine so as to prevent changes to the parameter potentially harmful to the patient. If the verification routine results in a positive result, the process of changing the parameter may move forward.

In a preferred embodiment, the hard key is directly wired to the safety central processing unit. The user interface also preferably comprises first, second and third hard keys, each of them directly wired to the safety central processing unit. The hard keys are preferably given a distinctive appearance so as to enable the user to identify each hard key with a distinct functional attribute, e.g., stop, confirm, or entry.

In another aspect of the invention, a method of operation of a dialysis machine is provided, the machine having a central computer control system and a user interface having a touch screen enabling a patient, by touching the touch screen, to select parametric values in a process of changing a parametric value pertinent to operation of the machine or to a dialysis treatment of a patient connected to the machine. The method comprises providing the user interface with at least one hard key and connecting the hard key directly to the central computer control system. After the user has selected the parametric value by touching the touch screen, the user is prompted to press the hard key to either (a) enter the parametric value selected, or, (b) if entry of the selected parametric value was accomplished by touching the touch screen, confirm the entry of the parametric value.

In accordance with the above method, a failure in the touch screen to respond to touching of the touch screen to either enter or confirm parametric value changes may be avoided.

In one embodiment of the invention, the central computer control system for the machine preferably includes host and safety CPUs, each comprising a microprocessor. The host and safety microprocessors each have has a first memory such as a random access memory (RAM) and a second memory, such as a hard disk, storing machine operation instructions and treatment prescriptions. In one aspect of the invention, a method is provided for using the touch screen, two hard keys, the first and second memories and host and safety microprocessors to change parameters to provide enhanced redundancy and safety capabilities and avoid single point failures in the touch screen, host microprocessor, or host memories. The method comprises the steps of:

a) touching the touch screen to select a parametric value;

b) pressing the first hard key to enter the selected parametric value, the computer system responsively storing the selected parametric value in the first memory is associated with the host microprocessor;

c) in response to pressing the first hard key, transmitting data associated with the selected value from the host microprocessor to the safety microprocessor and implementing a verification routine in the safety microprocessor. The safety microprocessor checks the parametric value for appropriateness for a patient connected to the machine so as to prevent changes from being implemented to the parameter potentially harmful to the patent.

d) If the verification routine has a positive result, the safety sends a signal back to the host microprocessor granting approval to the change and stores the changed parameter in its first memory. The touch screen then displays a message prompting the user to press the second hard key to confirm the change selected in step a).

e) If the user presses the second hard key to confirm the change, the host and safety microprocessors stores the new value in their respective second memories. The host and safety microprocessors then conduct a checking procedure to insure that the new value has been correctly stored in their second memories.

These and many other aspects and features of the invention will be more apparent from the following detailed description of preferred embodiments of the invention.

BRIEF DESCRIPTION OF THE DRAWINGS

In the following detailed description of presently preferred and alternative embodiments of the invention, reference will be made to the accompanying drawing figures, in which like reference numerals refer to like elements in the various views, and in which.

DETAILED DESCRIPTION OF THE PREFERRED EMBODIMENT

Figure 1:
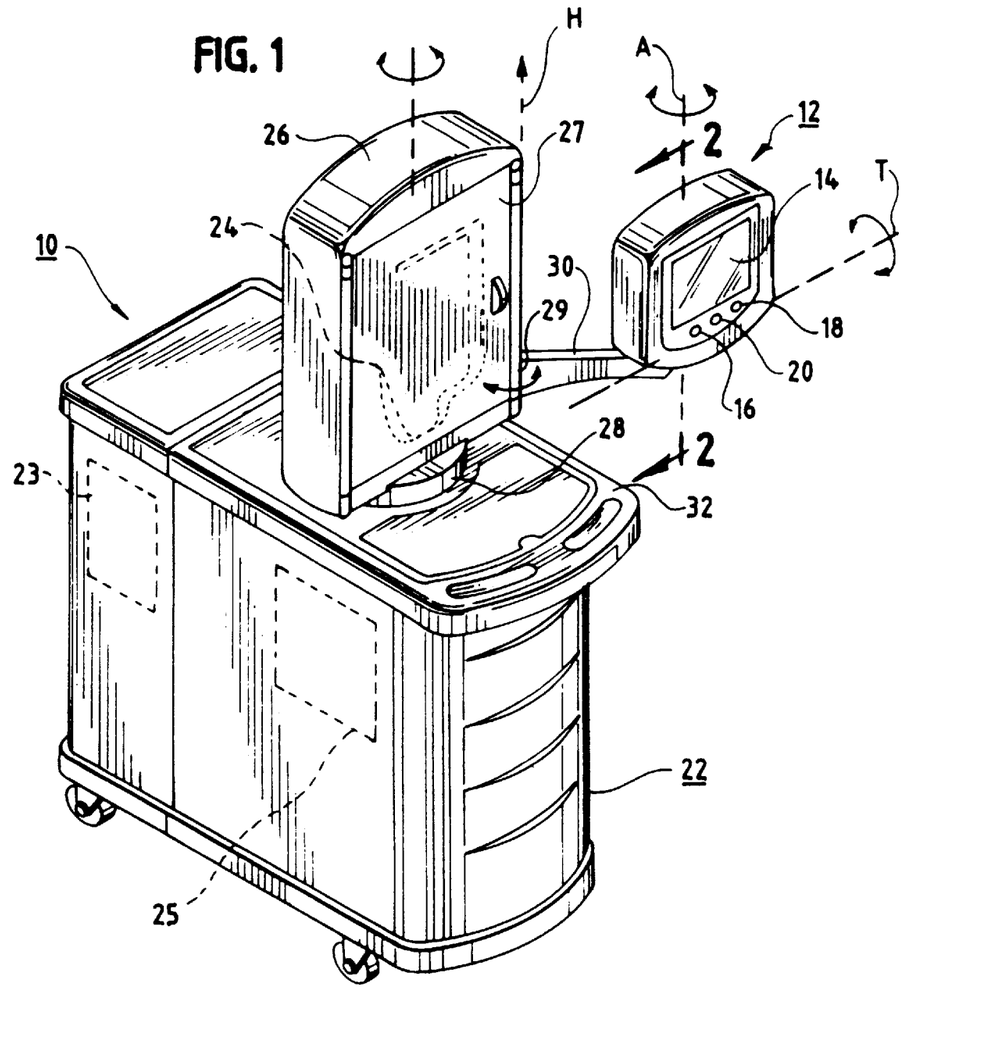
FIG. 1 is an illustration of a dialysis machine having a user interface in accordance with a preferred embodiment of the invention.

FIG. 1 is an illustration of a dialysis machine 10 having a user interface 12 which may be employed in practicing the invention. The dialysis machine 10 in the preferred embodiment is a machine suitable for use outside of a traditional dialysis clinic setting, such as the home, nursing home or self-care clinic environment. The user interface 12 is designed to be easy to use by a person other than a trained health care professional, such as the patient or a family member of the patient.

The preferred user interface 12 comprises a transparent touch screen 14, a display positioned immediately behind the touch screen 14, and a set of three hard keys or buttons 16, 18, 20 positioned below the touch screen 14. The touch screen 14 and hard keys 16, 18 and 20 are incorporated into a rigid housing 15 that is mounted to the distal end of a moveable arm 30.

Figure 2:
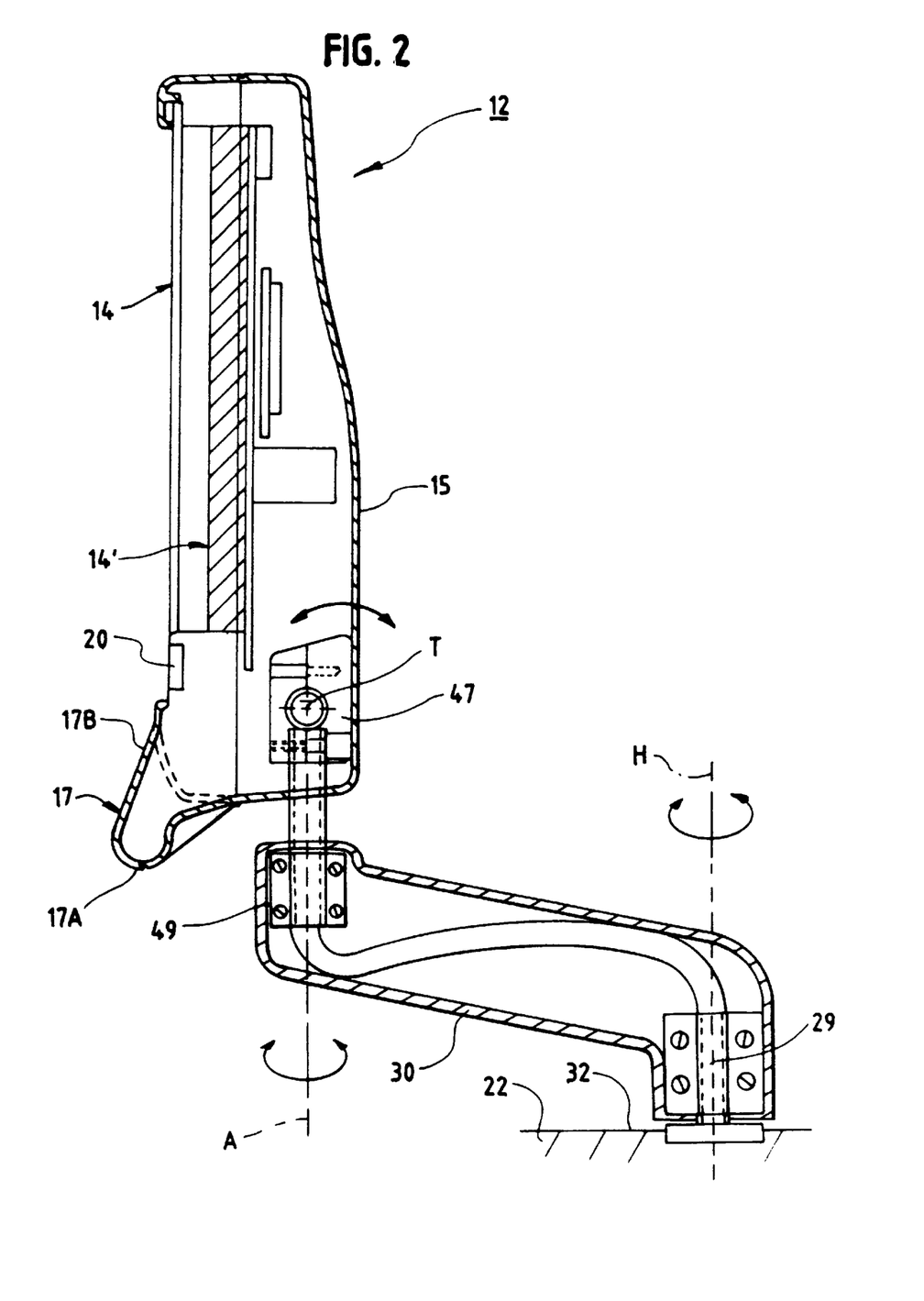
FIG. 2 is a cross-sectional view of the user interface in an embodiment in which the arm connecting the user interface to the machine is attached to the lower cabinet of the machine.
Figure 3:
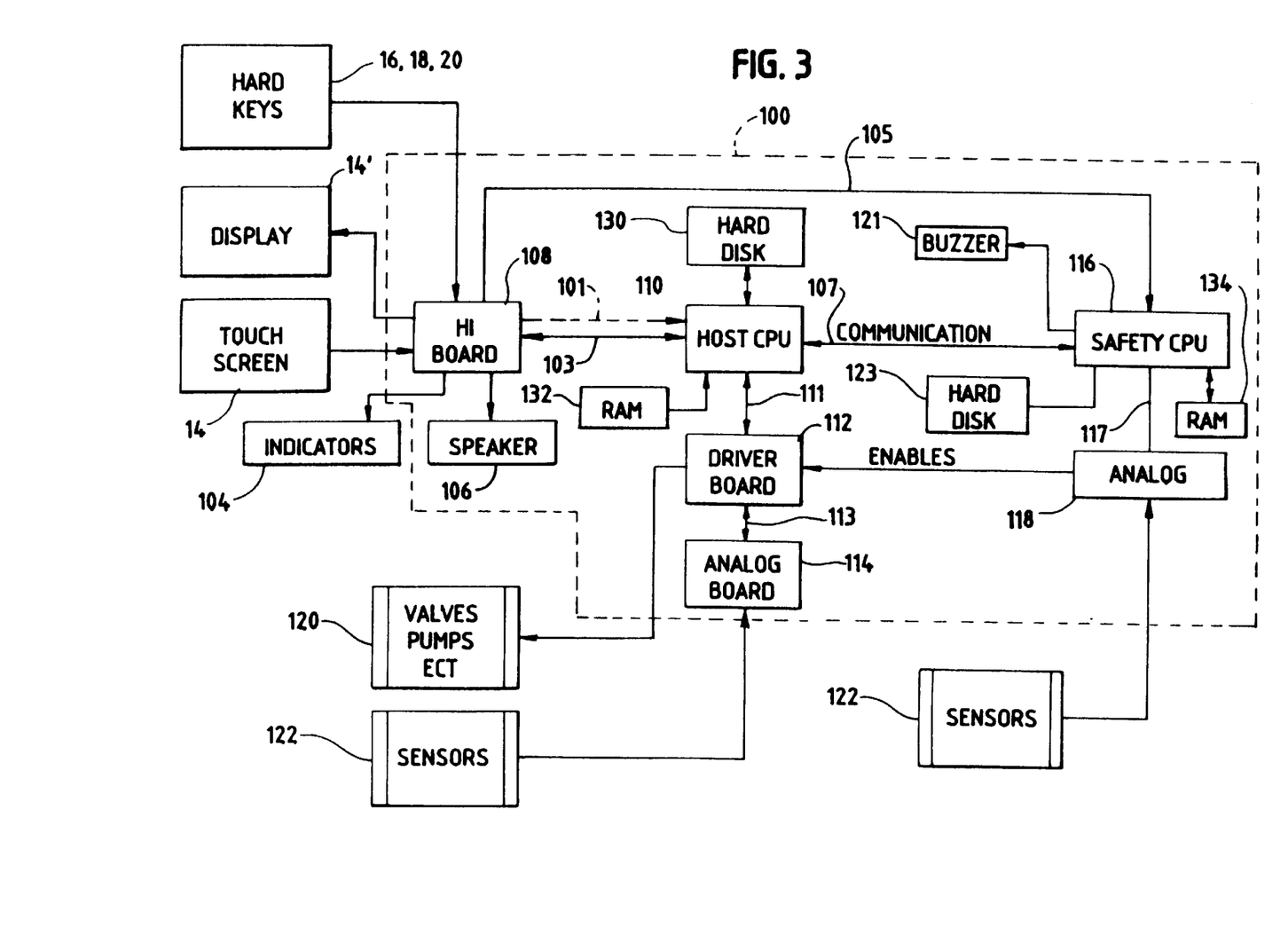
FIG. 3 is a block diagram of a control system governing the operation of the machine of FIG. 1.

The machine 10 has a central computer control system 100 shown in block diagram form in FIG. 3. The control system 100 is programmed to display information and messages to the patient or user of the machine on a display 14' (FIG. 2) immediately behind the touch screen surface 14. The control system 100, in cooperation with the hard keys 16, 18, 20 and touch screen 14, permits the user to change machine settings and enter information and otherwise control the operation of the machine before, during and after the treatment time.

The dialysis machine 10 of FIG. 1 has a water treatment module 23 and a dialysate preparation module 25 contained within the lower compartment 22 of the machine. These modules 23, 25 play no part in the present invention, and are described in detail in U.S. Pat. No. 5,591,344 to Kenley et al. and assigned to Aksys, Ltd., the assignee of the present invention, and in PCT application publication no. WO 96/25214. These references describe a preferred dialysis machine suitable for use in the home environment. The Kenley et al. U.S. Pat. No. 5,591,344 and published PCT application no. WO 96/25214 are both fully incorporated by reference herein. Additionally, the manner in which the dialysate solutions are prepared and circulated through the dialysate circuit is not particularly important to this invention and is well known in the art, and may be as described in the above-referenced Kenley et al. patent, or as described in the above-referenced Grogan et al. patent, or otherwise. Additionally, the user interface and method of operation is applicable to other types of medical instruments.

The dialysis machine 10 further includes an extracorporeal circuit 24 mounted above the lower cabinet 22. The extracorporeal circuit is housed behind a door 27 in an enclosure 26 that is mounted to a turntable 28. The turntable 28 is moveably mounted to the top of the lower cabinet 22 such that the turntable 28, enclosure 26 and extracorporeal circuit 24 are capable of rotation as a unit relative to the lower cabinet 22 about a vertical axis. The purpose of this rotation is to allow the extracorporeal circuit within the door 27 to be placed directly opposite a patient sitting next to the machine 10.

The details of the extracorporeal circuit 24 of the machine 10 of FIG. 1 are also not particularly germane to the present dialysis machine user interface. Blood is removed from the patient and introduced into an arterial line, and pumped by a blood pump to the blood chamber of a dialyzer. Blood-borne toxins and excess water are removed from the blood through the membrane of the dialyzer, and the blood is returned to the patient via a venous line. To prevent air from being introduced into the blood being returned to the patient, it is conventional in the dialysis art to place an air trap in the venous line. A method of using the user interface 12 to adjust the level in the air trap is described in a U.S. patent application of Rodney S. Kenley et al., Ser. No. 08/799,227, now U.S. Pat. No. 5,858,239, filed concurrently, which is incorporated by reference herein. Details of the extracorporeal circuit illustrated in FIG. 1 can be found in the published PCT application of Kenley et al., publication no. WO 96/25214 and in the Kenley et al. U.S. Pat. No. 5,591,344.

The proximal end of the moveable arm 30 may be either attached to the enclosure 26 via a hinge 29 as shown in FIG. 1, to the turntable 28, or to the lower cabinet 22 as shown in FIG. 2, such as to a corner of the upper surface of the lower cabinet, e.g., corner 32. Preferably, the user interface arm 30 is connected to the rest of the machine 10 via a hinge 29 or other suitable means such that the arm 30 can rotate about the vertical axis so as to position the user interface in a convenient orientation relative to a patient sitting or reclining next to the machine.

The user interface 12 of FIG. 1 is shown in cross section in FIG. 2, along the lines 2—2 of FIG. 1, in an embodiment in which the arm 30 is connected to the upper surface of the machine housing 22 at the corner 32. A hinge 29 connects the proximal end of the arm 30 to the housing 22 and allows the arm 30 to pivot about a vertical axis. A second hinge 49 at the distal portion of the arm 30 allows the user interface 12 to pivot about a vertical axis. A third hinge 47 in the user interface housing 15 allows the user interface 12 to tilt about a horizontal axis, i.e., to tilt down towards the patient if the patient is seated or reclining in bed, or up if the patient is standing.

The extreme lower portion of the user interface housing 15 has a lower handle portion 17 below the hard keys 16, 18, 20. The handle 17 has an extreme lower lip 17A that allows the user to grasp the interface housing 15, and a relatively large surface 17B extending across a substantial portion of the width of the housing that allows the user to push the user interface back, causing the arm 30 to move about the hinge 29, or rotate about the tilt hinge 47. The addition of a handle feature as described allows the user to interact with a specific portion of the user interface 12 away from the touch screen 14, whereby the user is less likely to push the touch screen 14 to move the touch screen about and accidentally operate the controls of the machine 10. The lower lip 17A and front surface 17B thus enable a user to manually manipulate the user interface housing 15 in a manner to cause rotation of the user interface about the housing axis H of FIGS. 1 and 3, the arm axis A, and the tilt axis T.

The front of the user interface housing 15 is substantially flat and includes the substantially transparent touch screen 14 per se. The display 14' for the touch screen is placed within the housing immediately behind the touch screen 14. The hard keys 16, 18, 30 are built into the front surface of the housing 15 immediately below the touch screen 14.

FIG. 3 is a block diagram of a computer control system module 100 installed in the lower cabinet 22 of the machine 10 that governs the operation of the machine. The use of a central computer control module to control active components of a dialysis machine is well known in the art and described in the above-referenced Kenley et al. and Grogan et al. patents. The module 100 controls the operation of the touch screen display 14' to display messages and information concerning the status of the machine and treatment. The module 100 operates the touch screen display 14' to prompt the user to touch the touch screen 14 and the hard keys 16, 18 in the process of changing parameters or inputting information into the computer system 100.

The touch screen 14 interfaces with the patient or other user and is provided for inputting commands or information from the patient into a human interface (HI) board 108 and displaying messages on the display 14' immediately behind the touch screen 14 surface in response to commands from a host Central Processing Unit (CPU) 110 from the HI board 108.

The hard keys 16, 18 and 20 are each a pair of physical, electrically isolated switches. One switch in each of the hard keys 16, 18, and 20 is preferably directly connected, and essentially hard wired, to a backup or safety CPU 116, and the other switch in the hard keys is connected to a host CPU 110. The switch for the emergency stop hard key 20 for the host CPU 110 is preferably directly connected to host CPU 110 from the HI board 108 over a separate conductor, as shown by the dashed line 101.

While FIG. 3 shows the connection between the hard keys 16, 18 and 20 going to the safety CPU 116 via the HI board 108 and conductor 105, the connection between the hard keys and the safety CPU 116 is considered a direct connection since the only function performed by the HI board 108 is debouncing and electrical interfacing the switch signals before they are sent to the Safety CPU 116. The connection is also considered a "direct connection" in the sense the signal path is intentionally designed to not share any circuitry with the Host CPU 110 or the microprocessor on the HI board 108.

The switch for the Red hard key 20 that is directed to the host CPU 110 is directly connected to the host CPU via the HI board 108, which performs debouncing and electrical interfacing, but the circuit does not share any other circuitry on the HI board 108 and the status of the switch is sent to the host CPU over the conductor 101 as described above. The switch for the host CPU 110 for the green and blue hard keys 18 and 16, respectively, are subject to debouncing by the microprocessor on the HI board 108, and the status of the switches is sent over the bus 103.

A set of indicators 104, including lights and audio indicators, a buzzer 121, and a speaker 106, alert the patient to abnormal conditions in the machine 10, and provide information as to the status of the modes of operation of the machine. The indicators 104 receive input signals from the host or safety CPU via the HI board 108. The buzzer 121 receives input signals from the safety CPU 116. Thus, audio and visual alarm activities are split among the two microprocessors 110, 116 in case one of them fails to work properly.

The host CPU 110 is connected via high speed digital data busses 111 and 113 to a driver board 112 and an analog board 114. The host CPU 110 comprises a microprocessor and implements a software program governing the operation of the machine stored in a hard disk memory 130 or a read only memory (not shown). The hard disk 130 stores other operational information, such as the patient's prescription, data from the passive components, and data input from the patient via the touch screen. An analog board 114 contains analog to digital converters for converting incoming analog signals from the passive sensors in the machine 22 (such as thermistors, pressure sensors and conductivity cells) into digital signals. The driver board 112 receives commands from the CPU 110 and sends the commands to the valves, pumps, heaters, motors, and other active components of the machine (represented by 120) to cause the components to change their status, e.g., commence or cease operation or change rate, as in the case of a pump, or open and close, as in the case of a valve. The signals from the passive components 122 of the system, for example, the conductivity sensors, pressure transducers, thermistors, etc. provide their inputs to the analog boards 114 and 118. The CPU 110 and driver board 112 together act as a controller for the active components.

The analog board 118 provides digital information on a bus 117 to the safety CPU 116. The safety CPU 116 comprises a microprocessor and acts as watchdog of critical system sensors, and provides enable signals to the driver 112 that allow certain driver commands to issue to the active components 120 (such as signals to the valve and air pump to raise or lower the level in the drip chamber in the extracorporeal circuit). These features are described in more detail below as they relate to the changing of machine parameters. Communications between the safety CPU 116 and host CPU 110 are passed on data bus 107. The safety CPU 116 activates a buzzer or other suitable alarm 121 if certain alarm conditions are present in the machine.

Both the host and safety CPUs 110 and 116 have an associated random access memory 132 and 134, respectively, for use in processing input information from the touch screen 14, for temporary storage of data, and for performing other tasks. In a preferred embodiment, the host CPU 110 and hard disk 130 are based on an off-the-shelf IBM compatible personal computer platform based on an Intel 386 or 486 microprocessor, or the equivalent. A similar microprocessor platform may be used for the safety CPU 116. Of course, other types of microprocessor platforms may be used. The safety CPU 116 also has its own hard disk memory 123. Note that the Safety and Host CPUs 116 and 110 do not share a hard disk, but rather have their own hard disk, for safety and redundancy reasons.

The host CPU 110 preferably has a modem and telephone line interface, a local area network (LAN) gateway card and interface and/or an RS-232 serial port (not shown) for allowing the machine 10 to receive and send messages to remote locations by a suitable communication link. The choice of which type of input/output interface will depend on where the machine 10 is installed (e.g., the home (modem), in a hospital (LAN interface), in a nursing home (modem and/or RS-232 and/or LAN). Potential entities that may wish to access information from the machine include a physician or nurse, the machine manufacturer, a service technician, and a remote monitoring facility such as a central station monitoring a plurality of machines. Preferably, machine status and treatment information is stored in the hard disk 130 and is accessible to the outside via the modem and host CPU 110 using an interactive program running on the host CPU 110 and at the remote site. The host CPU computing platform 110 also preferably implements a Microsoft™ graphical user interface operating system, and also Internet access software to allow messages to be sent to and retrieved from the machine 10 via the Internet.

Figure 4:
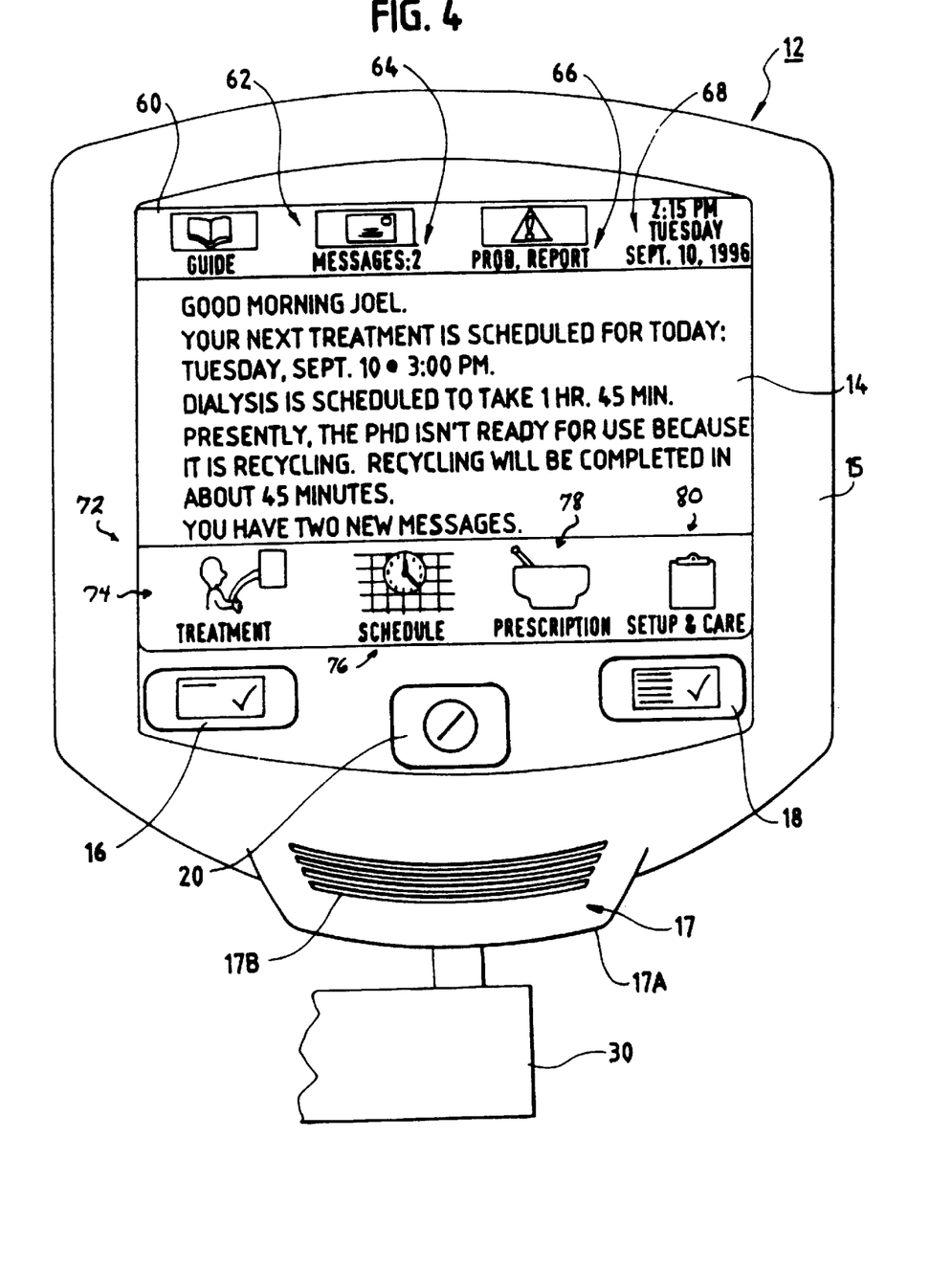
FIG. 4 is an elevational view of the user interface for the machine of FIG. 1, showing the general organization of the screen into discrete regions associated with different general functions.

FIG. 4 is an elevational view of the user interface 12 of FIG. 1 showing a display on the touch screen 14 that is used prior to the start of the treatment. The illustrated display, and preferably all of the displays for the user interface, is organized into discrete zones or portions extending across the width of the display. This organizational scheme assists the user to know where to look on the display for certain functions, icons, and information throughout all of the displays. One portion is preferably devoted to displaying instruction and status information to the user. Another is preferably devoted to displaying primary treatment and machine activities and functions. A third portion is preferably used for secondary machine activities and functions.

An embodiment of this general organizational scheme is shown in FIG. 4. The display has an upper portion 60 devoted to secondary activities and functions, and includes an icon 62 for a guide, which allows the user to gain information as to the machine when the icon 62 is pressed, a messages icon 64 indicating whether the patient has received new messages (e.g., via the Internet or public telephone network), and a problem report icon 66. The problem report icon 66 is a means for the machine to notify the patient of problems in a non-treatment mode. The screen display also has a time and day section 68.

The middle portion of the display 70 conveys status information to the patient, such as when the next treatment time is to begin. The portion 70 is given a paper pad type of look to reinforce the role played by this portion of the screen.

The lower portion 72 has a set of icons related to primary treatment and machine functions. These icons, when pressed, lead to additional screens that allow the patient to obtain information or enter data as to basic machine and treatment functions. These icons include an icon indicating treatment information 74, a dialysis schedule icon 76, a prescription icon 78 and a machine set-up icon 80.

When the user wishes to enter information into the machine from any of these menus, the user presses the touch screen 14 to navigate through various screen displays until they arrive at the appropriate screen for the action they wish to take.

As noted above, the user interface of FIG. 4 has at least one hard key (a physical button) positioned below the touch screen 14. Three hard keys are preferably provided, each with a distinctive visual appearance to assist the user to identify the hard key with a distinct functional attribute: a blue hard key 16, a green hard key 18 and a red hard key 20. The hard keys 16, 18 and 20 preferably consist of two electrically independent switches, one sending signals to the safety CPU 116 and the other sending signals to the HI board and host CPU 110 as described above.

The blue hard key 16 is connected to the host CPU 110 via the HI board 608, and is hard wired to the safety microprocessor 116. The blue hard key 16 is solely associated with an entry function. The user presses the blue hard key 16 when the user is finished editing a parameter during the process of changing parametric values for the machine. The blue hard key 16 is directly hard wired to the safety CPU 116 due to the fact that the safety CPU 116 is involved when parametric values are changed, as discussed below.

The green hard key 18 is a means for the user to confirm parametric value changes and some of the mode transitions of the machine 10. The green hard key 18 is connected to the host CPU 110 via the user interface software and hardware (i.e., HI board 108) and is hard wired to the safety CPU 116. The meaning associated with the pressing of the green hard key 18 also depends on the context of the current display and the current state of the machine 10. Due to safety considerations, the safety CPU 116 must have an independent means for determining the user's intention to change parametric values, i.e., independent of the touch screen or the host CPU, hence the green hard key 18 is directly connected and essentially hard wired to the safety CPU 116.

The red hard key 20 is a means for the user to issue an "Immediate Stop" command to the machine 10. The host and safety CPUs 110 and 116 respond by disabling a predetermined group of active components of the machine that leaves the machine in a patient-safe mechanically stopped condition. The meaning of the red hard key 20 is always the same regardless of the state of the machine 10. Unlike the blue and green hard keys, the red hard key 20 is directly connected and essentially hard wired to both the host and safety CPUs. Both microprocessors have the ability to disable the same group of active components, and will, redundant with each other, disable the active components.

As noted above, in order to assist the user to become familiar with the functions provided by the hard keys, they are preferably given a different color. Since one of the keys 20 is associated with an emergency stop function it is given a red color. The other keys 16 and 18 have more latitude in their selection of color, and we prefer to use a green key 18 to be generally identified with a confirmation function. The third key 16 is identified with an entry function, and is blue in the preferred embodiment. To assist further in reinforcing their different functions, they may be given different shapes, e.g., octagon, square and triangle. Other colors and shapes are of course possible.

Figure 5:
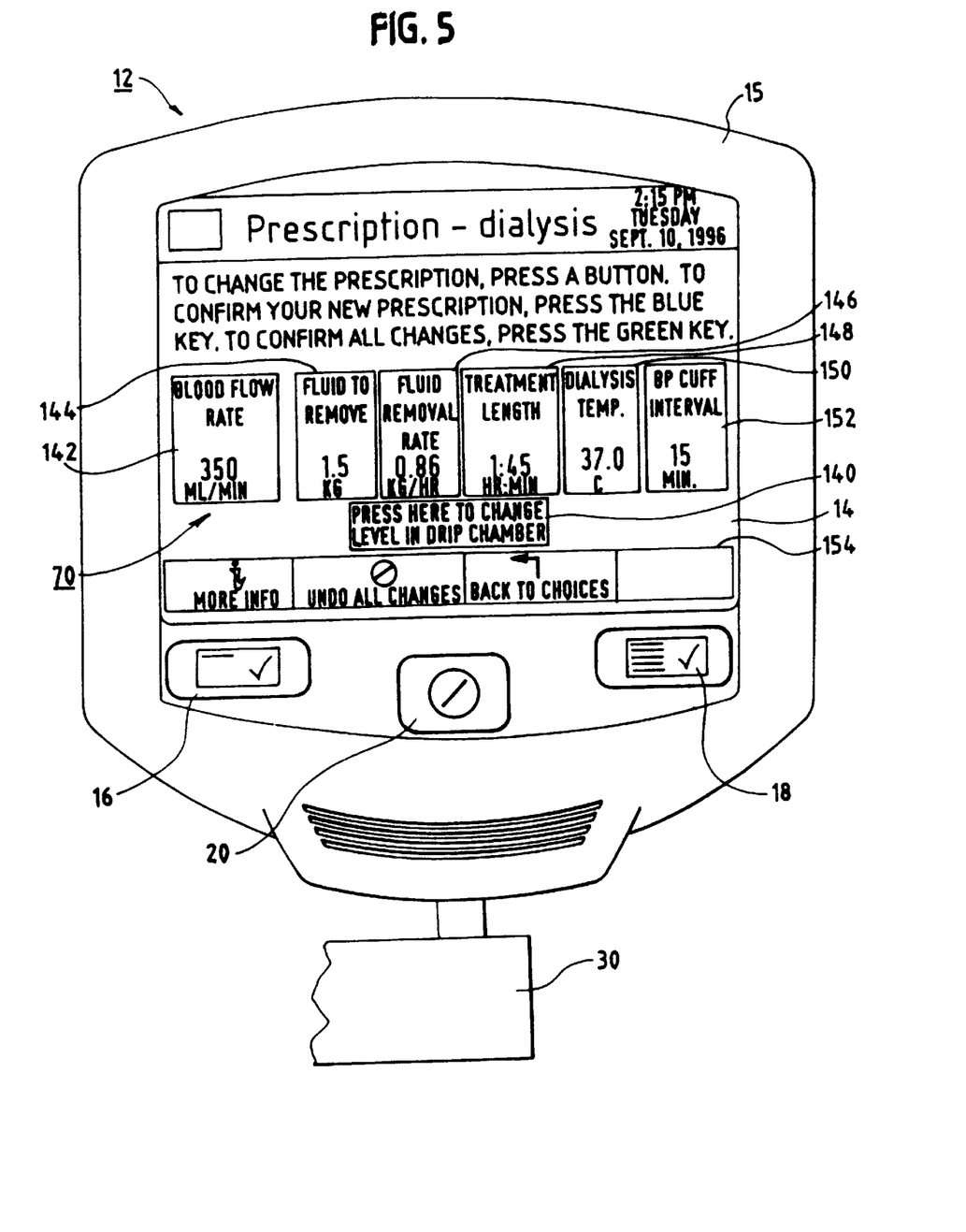
FIG. 5 is an illustration of the user interface of FIG. 4, with the touch screen displaying a dialysis prescription during a treatment session, the display requesting the patient to press an icon associated with a treatment parameter if they wish to change a parameter.

In accordance with the invention, the touch screen 14 and hard keys 16 and 18 are used in a process to adjust certain parameters pertinent to the operation of the machine or the dialysis treatment. FIG. 5 is an illustration of the user interface 12 showing a display on the touch screen 14 that can be accessed before or during the dialysis session. The touch screen 14 displays a message prompting a user to touch an icon 140 if they wish to change the level of the drip chamber in the extracorporeal circuit. When this icon 140 is pressed, an illustration of the blood drip chamber is displayed on the screen and the user indicates the current level in the illustration. The host CPU determines from the indicated level whether the level needs to rise or fall, and by approximately how much, to bring the level back to a predetermined desired level. This process and variations thereto are described in further detail in the above-referenced Kenley et al. patent application filed concurrently, Ser. No. 08/799,227, now U.S. Pat. No. 5,858, 239, incorporated by reference herein.

The display of FIG. 5 further includes several icons 142, 144, 146, 148, 150 and 152 that display current treatment settings in numerical form. The region 154 below the icons 142, 144, etc. can be used to display other information or to allow the patient to navigate to the previous screen or additional screens, obtain information, or report problems.

The display of FIG. 5 requests the patient to press an icon associated with a treatment parameter if they wish to initiate the process of changing the parameter. When the user presses an icon, for example, the treatment length icon 148, the display is modified to that shown in FIG. 6. Up and down arrows appear below the icons 142, 144, 146 et al. adjacent to the selected treatment parameter and the treatment parameter icon 148 is highlighted, e.g., made a brighter or a different color from the other icons. The user presses the up or down buttons 180, 182 to select the new value. The user then signifies that the editing is complete by pressing the blue hard key 16. After verification procedures are performed, the user is then prompted to confirm the change by pressing the green hard key 18.

In the preferred embodiment of the invention, the above process invokes operations with both the host and safety CPUs 110 and 116 to provide redundancy and safety features, which will now be described in detail in conjunction with FIGS. 3, 5 and 6.

The user touches one of icons 142, 144, 146, 148, 150 and 152 to indicate which parameter they wish to edit. A pair up and down arrows such as shown in FIG. 6 then appear. The user presses the up and down icons to select the new parametric value. In response to a prompt, the user indicates that the editing process is complete by pressing the blue hard key 16. An alternative would be to prompt the patient to press the green hard key, but this is a less desirable alternative since association of the green hard key 18 with a confirmation function would be diluted. A further possibility would be to press the activated icon, e.g., icon 144, a second time in response to a prompt. The preferred action of pressing the hard key 16 off the touch screen 14 initiates storage of the changed parametric value into the working RAM 132 for host CPU 110 (FIG. 3). A CRC (Cyclical Redundancy Check) value is calculated by the host CPU 110 for the set of parametric values currently displayed on the screen. The CRC check is calculated by the host CPU 110 only (at this point), and only in response to the pressing of the blue or entry hard key 16.

The following information is then sent from the host CPU 110 to the safety CPU 116 over the bus 107 in response to a pressing of the entry hard key 16: a unique screen identifier associated with the display currently on the touch screen 14, the current values of all the modifiable parameters displayed on the screen, a unique parameter identifier associated with the parameter to be changed, and the calculated CRC value. The data is stored in the Safety CPU 116's RAM 134.

The safety CPU 116 then performs a verification routine to determine that the requested change to the parameter is appropriate for the patient and is consistent with the current status of the machine 10 and current display, and prevent any changes that could be harmful to the patient. Specifically, in a preferred embodiment, the safety CPU 116 verifies that the screen displayed could be displayed given the current state of the machine 10. It also verifies that only one parametric value, of all the modifiable parametric values associated with the current screen, has changed. It also verifies that the parameter identified by the host microprocessor 110 is editable on the specified screen. If further verifies that the parameter that the host has identified as being the changed parameter is the same one identified by the safety CPU 116. This verification is done by the Safety CPU 116 using its own copy of the treatment information stored in its hard disk 123 and comparing this information with the information sent from the host CPU 110 to determine which parameter for the screen has changed. The safety CPU 116 further verifies that the parametric value that changed passes all range, resolution, format and other appropriate validation and safety tests. This is accomplished by comparing the proposed new value with stored values on the hard disk 123 associated with permissible range of values and other validation criteria for the patient. The values stored on the hard disk 123 may be either modifiable by a doctor's prescription loaded into the hard disk 123 or validation or safety criteria set at the time of machine manufacture. Finally, the safety CPU 116 calculates a CRC on the set of parametric values currently displayed and determines whether the CRC value matches the CRC value calculated by the host CPU 110. It will be appreciated that the above specific verification routine is not the only possible verification routine and can be modified to be more or less stringent for different parameters and states of the machine.

If the safety CPU 116 detects an error in the verification routine it notifies the host CPU 110 and treats the failure in a manner to that of a triggered protective system, such as by displaying an error message or activating one of the indicators 104 and/or the buzzer 121.

If the safety CPU 116 does not detect an error, it sends a signal to the host CPU 110 indicating the tests were passed and notifying the host 110 that the host 110 may continue. The safety CPU 116 transfers back to the host CPU 110 the data stored in RAM 134 that was forwarded from the host 110 (while keeping a copy in RAM 134), and the CRC calculated by the safety CPU. This data is stored in work space in the host CPU's RAM 132.

The host CPU 110 then compares the CRC calculated by the safety CPU 116 to the host's CRC value, compares all the parameter values returned by the safety CPU 116 to the values it originally sent, and treats any mismatch in a manner similar to that of a triggered protective system.

If the comparison is valid, then the host CPU 116 updates the screen display with the parametric values returned by the safety CPU and stored in RAM 132. The host CPU 110 then causes the touch screen 14 to display a prompt to the user that they must press the green hard key 18 to confirm the pending change to the displayed parametric value. Note that, up until this point, the data associated with the changed parameter is not yet loaded into the hard disk 130 that contains the program, and thus the machine cannot operate in accordance with the selected parametric value. Rather, a confirmation step must still occur, i.e., a pressing of the green hard key 18 off of the touch screen.

When the user presses the green hard key 18 to confirm the change, the host microprocessor calculates a new CRC file and then writes the RAM 132 copy of the parameters and the CRC to the hard disk 130. The safety CPU 116 simultaneously performs the same actions with its copy of the CRC and the parameters stored in RAM 134, writing the RAM copy and CRC value to its hard disk 123. Both host and safety CPUs will then reload their sets of parameter and CRC data into their respective RAM and verify with each other that the new CRC value agrees with each other. The host CPU 110 then removes the "Press the green key to confirm" prompt and enables a screen navigation prompt allowing the user to navigate through other screens. At this point, the user can either navigate off the screen of FIG. 6 or select another parameter for editing. The changing of the parametric value is now complete since the parametric value data is loaded into the hard disks of the host and safety CPU.

Figure 6:
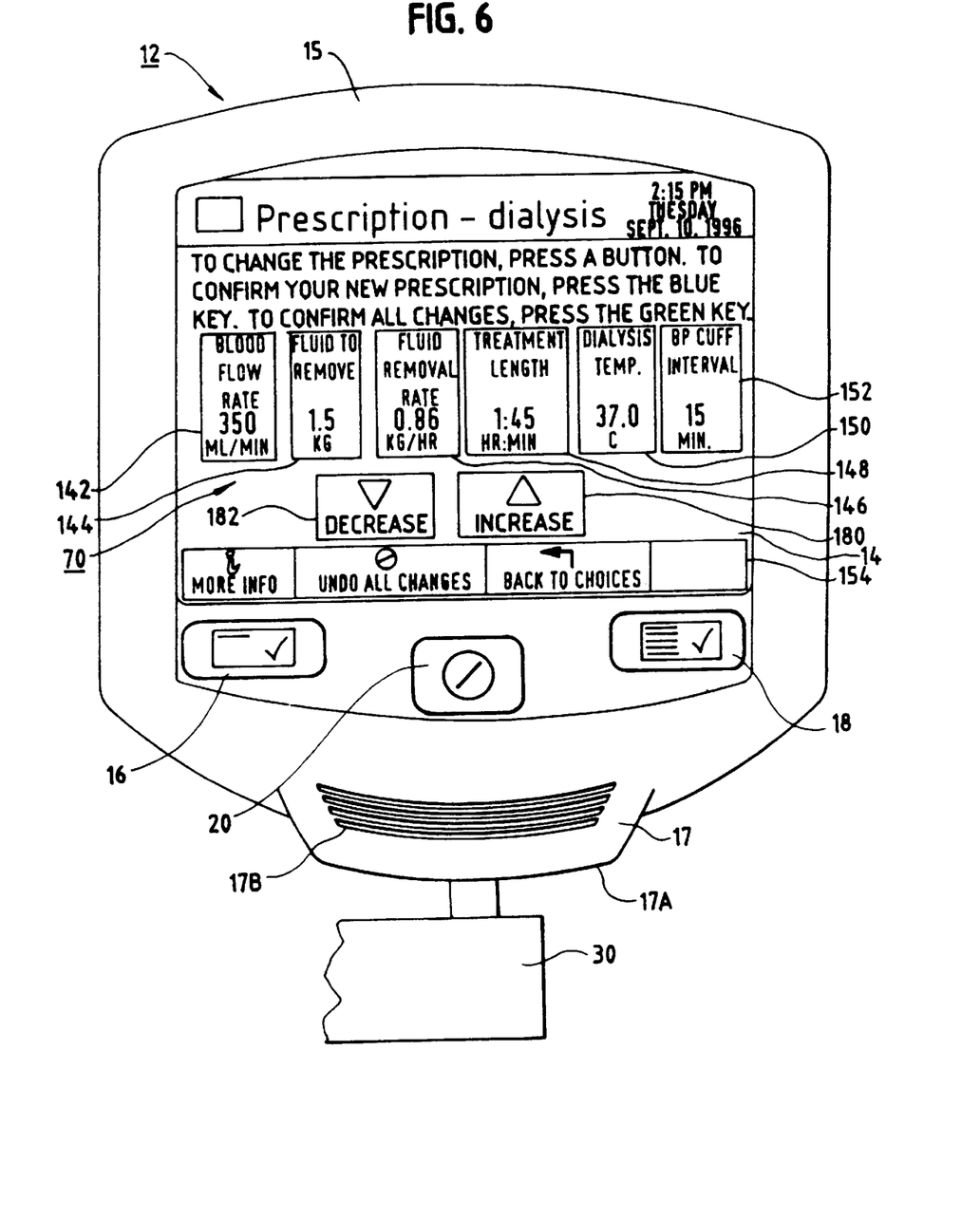
FIG. 6 is an illustration of the user interface of FIG. 1 after the user has pressed the icon shown in FIG. 5, showing up and down arrows that permit the user to select a different value for the treatment parameter.

While the above discussion has assumed that the user only modifies one of the several parameters from the display of FIG. 6, the user may choose to modify another parameter on the same screen after the blue hard key 16 has been pressed. The user does not have to press the green hard key for every single parameter change. For example, the user may select a new blood flow rate (using icon 142), then press the blue hard key 16 to signify completing of the editing process, select a new fluid removal rate (using icon 146), then press the blue hard key 16, then edit the dialysate temperature (using icon 150), and then press the blue hard key 16. After each pressing of the blue hard key 16, the above-described verification routine is performed. If the verification routine results in a positive result for each pressing of the blue hard key, the display will continue to display a "press the Green hard key to confirm" prompt. The user will press the green hard key once to confirm that they intend to change all the parametric values that have been selected.

Since the new updated parametric value(s) are now entered into the hard disk memory 130, the host CPU 110 commands the relevant active components of the machine 10 in accordance with the new parametric value.

This use of the hard keys in the process of changing parametric values is considered to be distinctly different and an improvement from merely touching the touch screen to enter or change values, since the touch screen can be prone to failures. Failures in a touch screen to properly respond to a touching of the surface can arise in a variety of ways, such from mechanical failures due to repeated use over a prolonged period of time, the screen surface material taking on a depression or set in a particular area from repeated use, electro-static shock causing the grid to fail in particular area, high electromagnetic fields causing the contacts to touch, cleaning agents leaking around the periphery of the screen, and so on. By also using hard keys or physical switches directly wired to the host and safety CPU to change values, the microprocessors have an independent means for determining whether the user has entered values or intends to confirm the changes. Further, by virtue of connecting the hard keys to both microprocessors, and using the pairs of redundant host and safety memories to check against each other, a failure in either microprocessor or associated memories will be detected, allowing for alarms or other protective action to be initiated while maintaining patient safety.

The above-described method of using the touch screen and hard keys to change machine or treatment parameters is also applicable to changing operational modes in the machine. For example, if the machine 10 is in a prepare dialysate solution mode, the display 14 may display a prompt indicating that the user should press the green hard key to indicate that they are ready to enter into a prepare access site mode or a dialyze mode. Another example would be when the user is finishing the dialysis session and indicates to the machine that they are ready to end dialysis and begin a rinseback mode. The user is prompted to press a hard key (e.g., the green hard key) to indicate that they wish to confirm that they are ready to start the next mode of operation. Further, by virtue of the connection of the hard keys to both the host and safety CPUs, a verification routing can be performed by both CPUs to confirm that the machine is in a state where the change is mode is safe for the patient.

For some mode changes, it is presently contemplated that little or no user interaction with the machine is necessary. For example, the transition from a clean and rinse mode to a prepare dialysate solution mode may be made without requiring user involvement. However, the current mode of operation is preferably communicated to the patient, such as by displaying a message telling the user what mode the machine is in (e.g., clean and rinse mode) and an illustration communicating how much time remains until the machine has completed the present mode.

It will be appreciated that various modifications may be made to the methods described herein without departure from the true scope and spirit of the invention. Furthermore, as used in the claims, the term "touch screen" is intended to mean the combination of the transparent physical surface touched by the user and the display immediately behind the surface touched by the user. The term "hard key", as used in the claims, is not intended to be limited to a button or key having two physical switches directed to host and safety CPUs, but rather, unless otherwise stated, is intended to mean simply a manually manipulable physical switch off of the touch screen such as a button operatively connected to a central computer system for the medical instrument. This true scope and spirit is defined by the appended claims, interpreted in light of the foregoing specification.

We claim:

1. A dialysis machine, comprising:
   a cabinet enclosing hydraulic circuitry for preparation of a dialysate solution therein;
   an extracorporeal circuit module contained in an enclosure that is rotatably mounted to said cabinet, wherein a user of said dialysis machine may rotate said extracorporeal circuit module about an axis in a multitude of different orientations relative to said cabinet, said extracorporeal circuit enclosure further housing a blood pump and a dialyzer, and
   an elongate arm having a first proximal end rotatably connected to either said cabinet or to said extracorporeal circuit enclosure and a second distal end, and wherein said second distal end has mounted thereto a user interface having a screen display, said user interface allowing patient or treatment information to be entered into a computer control system for said dialysis machine, said first proximal end capable of rotation with respect to either said cabinet or said extracorporeal circuit enclosure; and
   wherein said user interface is mounted to said second distal end of said arm in a manner such that said user interface may be rotated about at least one horizontal axis and about at least one vertical axis to thereby orient said screen display in a multitude of different positions relative to said second distal end of said arm.

2. The dialysis machine of claim 1, wherein said cabinet comprises a top surface and wherein said first end of said arm is mounted to said top surface of said cabinet with a hinge, said hinge permitting said arm to rotate relative to said cabinet about a vertical axis.

3. The dialysis machine of claim 1, wherein said first end of said arm is mounted to said extracorporeal circuit module by a hinge, said hinge permitting said arm to rotate relative to said extracorporeal circuit about a vertical axis.

4. The dialysis machine of claim 1, wherein said user interface is mounted to said second distal end of said arm by first and second hinges, said first hinge permitting said user interface to rotate relative to said arm about a vertical axis, said second hinge permitting said user interface to rotate relative to said arm about a horizontal axis.

5. The dialysis machine of claim 1, wherein said user interface comprises a touch screen.

6. The dialysis machine of claim 1, wherein said cabinet comprises a substantially planar top surface and a corner formed at the intersection of a side portion and an end portion of said top surface, and wherein said first proximal end of said arm is mounted at said corner portion of said top surface of said cabinet.

7. A dialysis machine, comprising:
   a cabinet enclosing hydraulic circuitry for preparation of a dialysate solution therein;
   an extracorporeal circuit module rotatably mounted to said cabinet, wherein a user of said dialysis machine may rotate said extracorporeal circuit module about an axis in a multitude of different orientations relative to said cabinet, said extracorporeal circuit module comprising an enclosure for housing a blood pump and a dialyzer, and
   an elongate arm having a first proximal end connected to either said cabinet or to said extracorporeal circuit module and a second distal end, and wherein said second distal end has mounted thereto a user interface having a screen display, said user interface allowing patient or treatment information to be entered into a computer control system for said dialysis machine; and
   wherein said user interface is mounted to said second distal end of said arm in a manner such that said user interface may be rotated about at least one axis to thereby orient said screen display in a multitude of different positions relative to said second distal end of said arm,
   wherein said user interface comprises a touch screen and at least three hard keys placed adjacent to said touch screen, including a first hard key associated with an emergency stop function for said dialysis machine, a second hard key associated with an entry function in operation of said touch screen, and a third hard key associated with a confirm function in operation of said touch screen.

8. A dialysis machine, comprising:
   a cabinet enclosing hydraulic circuitry for preparation of a dialysate solution therein;
   an extracorporeal circuit module rotatably mounted to said cabinet, wherein a user of said dialysis machine may rotate said extracorporeal circuit module about an axis in a multitude of different orientations relative to said cabinet, said extracorporeal circuit module comprising an enclosure for housing a blood pump and a dialyzer, and
   an elongate arm having a first proximal end connected to either said cabinet or to said extracorporeal circuit module and a second distal end, and wherein said second distal end has mounted thereto a user interface having a screen display, said user interface allowing patient or treatment information to be entered into a computer control system for said dialysis machine; and
   wherein said user interface is mounted to said second distal end of said arm in a manner such that said user interface may be rotated about at least one axis to thereby orient said screen display in a multitude of different positions relative to said second distal end of said arm,
   wherein said user interface comprises:
   1) a touch screen displaying messages and information as to said dialysis machine to a user and permitting said user to touch said touch screen to select at least one parametric value pertinent to operation of said dialysis machine or pertinent to a treatment by said dialysis machine, and 2) at least one hard key off of said touch screen, said touch screen prompting said user to press said hard key to signify that the selection of said at least one parametric value by said user has been completed;

and wherein said dialysis machine further comprises a computer control system controlling the operation of said dialysis machine and responsive to said touch screen and said at least one hard key, said control system comprising a host microprocessor and a safety microprocessor operatively connected to each other so as to enable an exchange of information related to said at least one selected parametric value, wherein said pressing of said hard key causes said host and safety microprocessors to undergo a verification routine whereby said selected parametric value is checked for appropriateness for a patient connected to said machine so as to prevent changes to said parameter potentially harmful to said patient.

* * * * *